United States Patent
Sudol et al.

(10) Patent No.: US 9,943,287 B2
(45) Date of Patent: Apr. 17, 2018

(54) HIGH POROSITY ACOUSTIC BACKING WITH HIGH THERMAL CONDUCTIVITY FOR ULTRASOUND TRANSDUCER ARRAY

(75) Inventors: Wojtek Sudol, Eindhoven (NL); Kevin Grayson Wickline, Eindhoven (NL); Yongjian Yu, Eindhoven (NL); Heather Beck Knowles, Eindhoven (NL); James Paolino, Eindhoven (NL); Richard Edward Davidsen, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 116 days.

(21) Appl. No.: 14/003,240

(22) PCT Filed: Mar. 14, 2012

(86) PCT No.: PCT/IB2012/051208
§ 371 (c)(1),
(2), (4) Date: Sep. 5, 2013

(87) PCT Pub. No.: WO2012/123908
PCT Pub. Date: Sep. 20, 2012

(65) Prior Publication Data
US 2013/0345567 A1    Dec. 26, 2013

Related U.S. Application Data

(60) Provisional application No. 61/453,690, filed on Mar. 17, 2011.

(51) Int. Cl.
*A61B 8/00* (2006.01)
*B06B 1/06* (2006.01)
*G10K 11/00* (2006.01)

(52) U.S. Cl.
CPC .......... *A61B 8/4494* (2013.01); *A61B 8/4483* (2013.01); *B06B 1/0629* (2013.01); *G10K 11/002* (2013.01)

(58) Field of Classification Search
CPC .... A61B 8/14; A61B 8/00; B06B 1/06; G01N 29/00
See application file for complete search history.

(56) References Cited

U.S. PATENT DOCUMENTS 3,995,179 A * 11/1976 Flournoy ............. G10K 11/002
310/335
4,297,607 A * 10/1981 Lynnworth ............. B06B 1/067
310/327

(Continued)

FOREIGN PATENT DOCUMENTS

JP    2000165995 A    6/2000
JP    2010258602 A    11/2010

(Continued)

*Primary Examiner* — Tse Chen
*Assistant Examiner* — Nate S Sunwoo

(57) ABSTRACT

A backing block for an ultrasonic transducer array stack of an ultrasound probe is formed as a composite structure of graphite foam impregnated with an epoxy resin. The epoxy resin penetrates the porous foam structure at least part-way into the depth of the graphite foam block and, when cured, provides the backing block with good structural stability. The composite graphite foam backing block is bonded to the integrated circuit of a transducer to provide high thermal conductivity away from the transducer and good acoustic attenuation or scattering of rearward acoustic reverberations.

20 Claims, 5 Drawing Sheets

(56) References Cited

U.S. PATENT DOCUMENTS

| | | | |
|---|---|---|---|
| 5,329,498 A | 7/1994 | Greenstein | |
| 5,541,567 A * | 7/1996 | Fogel | H01F 17/0006 174/260 |
| 5,560,362 A | 10/1996 | Sliwa | |
| 5,648,941 A | 7/1997 | King | |
| 5,722,412 A * | 3/1998 | Pflugrath | A61B 8/00 600/441 |
| 6,551,247 B2 | 4/2003 | Saito et al. | |
| 6,673,328 B1 * | 1/2004 | Klett | C04B 38/00 423/445 R |
| 7,348,713 B2 | 3/2008 | Hashimoto | |
| 7,567,016 B2 | 7/2009 | Lu et al. | |
| 7,755,255 B2 | 7/2010 | Saito et al. | |
| 8,093,782 B1 * | 1/2012 | Hossack | G10K 11/002 310/326 |
| 8,232,705 B2 | 7/2012 | Tai | |
| 8,376,950 B2 | 2/2013 | Nagano et al. | |
| 8,611,490 B2 | 12/2013 | Zhang | |
| 2002/0136680 A1 * | 9/2002 | Kanno | C04B 38/0022 423/445 R |
| 2003/0029010 A1 * | 2/2003 | Aime | G10K 11/002 29/25.35 |
| 2003/0032884 A1 | 2/2003 | Smith et al. | |
| 2004/0100163 A1 | 5/2004 | Baumgartner et al. | |
| 2005/0099096 A1 * | 5/2005 | Baumgartner | B06B 1/0622 310/334 |
| 2005/0263516 A1 * | 12/2005 | Natsuhara | F27B 17/0025 219/385 |
| 2005/0275313 A1 | 12/2005 | Yamashita et al. | |
| 2006/0084966 A1 | 4/2006 | Maguire et al. | |
| 2006/0261707 A1 * | 11/2006 | Wildes | A61B 8/546 310/346 |
| 2008/0098816 A1 * | 5/2008 | Yamashita | G10K 11/002 73/596 |
| 2008/0188755 A1 | 8/2008 | Hart | |
| 2008/0243001 A1 * | 10/2008 | Oakley | A61B 8/4281 600/459 |
| 2008/0315724 A1 * | 12/2008 | Kunkel, III | B06B 1/0633 310/334 |
| 2009/0000383 A1 * | 1/2009 | Knowles | G10K 11/02 73/632 |
| 2009/0062656 A1 * | 3/2009 | Hyuga | A61B 8/12 600/459 |
| 2010/0168581 A1 | 7/2010 | Knowles et al. | |
| 2011/0181149 A1 | 7/2011 | Shikata | |
| 2011/0198151 A1 | 8/2011 | Oakley et al. | |
| 2012/0181902 A1 | 7/2012 | Gelly et al. | |
| 2013/0114379 A1 * | 5/2013 | Fischer | G10K 11/165 367/189 |

FOREIGN PATENT DOCUMENTS

| | | |
|---|---|---|
| WO | 2008121238 A2 | 10/2008 |
| WO | 2009083896 A2 | 7/2009 |

* cited by examiner

HIGH POROSITY ACOUSTIC BACKING WITH HIGH THERMAL CONDUCTIVITY FOR ULTRASOUND TRANSDUCER ARRAY

CROSS-REFERENCE TO PRIOR APPLICATIONS

This application is a U.S. National Phase application under 35 U.S.C. § 371 of International Application No. PCT/IB2012/051208, filed on Mar. 14, 2012, which claims the benefit &U.S. Provisional Patent Application No. 61/453,690, filed on Mar. 17, 2011. These applications are hereby incorporated by reference herein.

This invention relates to medical diagnostic ultrasound systems and, in particular, to backing materials for an ultrasonic transducer array.

Two dimensional array transducers are used in ultrasonic imaging to scan in three dimensions. Two dimensional arrays have numerous rows and columns of transducer elements in both the azimuth and elevation directions, which would require a large number of cable conductors to couple signals between the probe and the mainframe ultrasound system. A preferred technique for minimizing the number of signal conductors in the probe cable is to perform at least some of the beamforming in the probe in a microbeamformer ASIC (application specific integrated circuit.) This technique requires only a relatively few number of partially beamformed signals to be coupled to the mainframe ultrasound system, thereby reducing the required number of signal conductors in the cable. However a large number of signal connections must be made between the two dimensional array and the microbeamformer ASIC. An efficient way to make these connections is to design the transducer array and the ASIC to have flip-chip interconnections, whereby conductive pads of the transducer array are bump bonded directly to corresponding conductive pads of the ASIC.

The high density electronic circuitry of the microbeamformer ASIC can, however, produce a significant amount of heat in its small IC package, which must be dissipated. There are two main directions in which this heat can flow. One direction is forward through the acoustic stack toward the lens at the patient-contacting end of the probe. Thermal conductivity is aided in this direction by electrically conductive elements in the transducer stack. This forward path exhibits relatively low resistance to thermal flow. Build-up of heat in the lens must then be prevented by reducing transmission voltage and/or the pulse repetition frequency, which adversely affects probe performance.

The preferred thermal conduction direction is to the rear, away from the lens and toward a heat spreader (typically aluminum) at the rear of the probe. But generally located behind the transducer stack, the array elements and the microbeamformer ASIC, is an acoustic backing block. The purpose of the acoustic backing block is to attenuate ultrasonic energy emanating from the rear of the acoustic stack and prevent this energy from causing reverberations that are reflected toward the acoustic stack. An acoustic backing block is generally made of a material with good acoustic attenuation properties such as an epoxy loaded with microballoons or other sound-deadening particles. Although many epoxy-filler composite backings have been developed to isolate the ASICs from the supporting structure (usually aluminum) of the probe assembly, they have two disadvantages. If formulated to have high attenuation then they have unacceptable thermal conductance. If formulated to have high thermal conductivity they have unacceptable attenuation. Hence it is desirable to provide an acoustic backing block for an ultrasound probe which exhibits good acoustic attenuation of acoustic energy entering the block, good thermal conductivity toward the rear of the probe and away from the lens, good structural stability which can support the acoustic stack as needed, and appropriate electrical isolation of the microbeamformer ASIC from other conductive components of the probe.

In accordance with the principles of the present invention, a backing block for an ultrasonic transducer array stack is formed of a porous graphite foam material which has high acoustic attenuation and high thermal conductivity. In a preferred implementation the foam backing block is constructed as a composite with the foam structure filled with an epoxy resin. An electrically isolating layer can be located on the top of the backing block at the bond between the backing block and the ASIC of the acoustic stack assembly.

Figure 1:
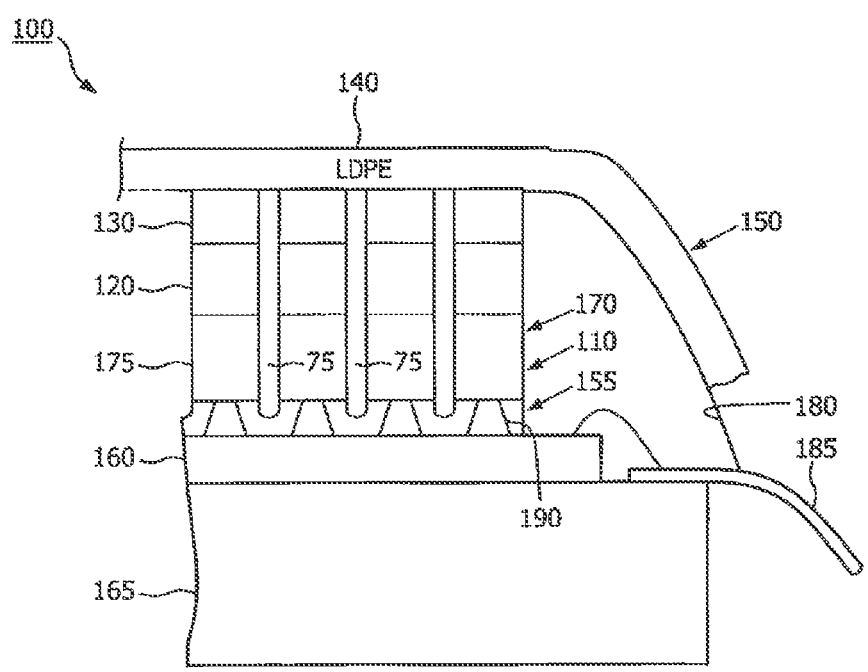
FIG. 1 illustrates an acoustic stack with a thermally conductive backing block constructed in accordance with the principles of the present invention.

Referring first to FIG. 1, an acoustic stack 100 with a thermally conductive backing block which is constructed in accordance with the principles of the present invention is shown schematically. A piezoelectric layer 110 such as PZT and two matching layers bonded to the piezoelectric layer are diced by dicing cuts 75 to form an array 170 of individual transducer elements 175, four of which are seen in FIG. 1. The array 170 may comprise a single row of transducer elements (a 1-D array) or be diced in two orthogonal directions to form a two-dimensional (2D) matrix array of transducer elements. The matching layers match the acoustic impedance of the piezoelectric material to that of the body being diagnosed, generally in steps of progressive matching layers. In this example the first matching layer 120 is formed as an electrically conductive graphite composite and the second matching layer 130 is formed of a polymer loaded with electrically conductive particles. A ground plane 180 is bonded to the top of the second matching layer, and is formed as a conductive layer on a film 150 of low density polyethylene (LDPE) 140. The ground plane is electrically coupled to the transducer elements through the electrically conductive matching layers and is connected to a ground conductor of flex circuit 185. The LDPE film 150 forms the third and final matching layer 140 of the stack.

Below the transducer elements is an integrated circuit 160, an ASIC, which provides transmit signals for the transducer elements 175 and receives and processes signals from the elements. Conductive pads on the upper surface of the integrated circuit 160 are electrically coupled to conductive pads on the bottoms of the transducer elements by stud bumps 190, which may be formed of solder or conductive epoxy. Signals are provided to and from the integrated circuit 160 by connections to the flex circuit 185. Below the integrated circuit 160 is a backing block 165 which attenuates acoustic energy emanating from the bottom of the transducer stack. In accordance with the principles of the present invention, the backing block also conducts heat generated by the integrated circuit away from the integrated circuit and the transducer stack and away from the patient-contacting end of the transducer probe.

Figure 2:
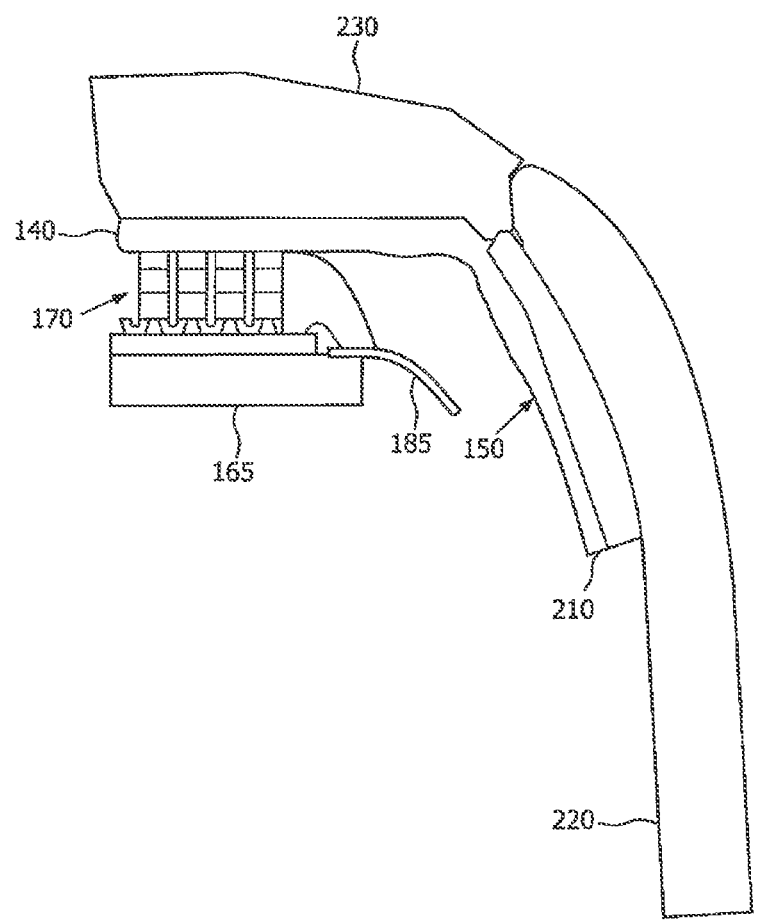
FIG. 2 illustrates the acoustic stack of FIG. 1 when assembled in a transducer probe with a lens cover.

FIG. 2 illustrates the transducer stack assembly of FIG. 1 when assembled inside a transducer probe. In the probe of FIG. 2 the third matching layer 140 is bonded to the acoustic lens 230. Ultrasound waves are transmitted through the lens 230 and into the patient's body during imaging, and echoes received in response to these waves are received by the transducer stack through the lens 230. The LDPE film 150 serves to enclose the transducer stack in this embodiment as it is wrapped around the stack and bonded by an epoxy bond 210 to the probe housing 220. Further details of this construction are found in US patent publication no. US 2010/0168581 (Knowles et al.)

A preferred implementation for the backing block 165 is illustrated in the remaining drawings. A preferred backing block 165 starts with a block of graphite 20. Other alternatives include graphite loaded with metals such as nickel or copper which provide good machinability and favorable thermal properties. The graphite block 20 is used to form a composite backing structure which satisfies a number of performance objectives. First, the backing structure must have good Z-axis thermal conductivity. Graphite has good thermal conductivity, a Tc of 80 to 240 W/m° K at 0° C.-100° C. For conduction parallel to the crystal layers, Tc will approach 1950 W/m° K at 300° K. The Z-axis direction is the direction back and away from the transducer stack 100 and the integrated circuit 160. Thus, it is desirable to align the crystal layers of the graphite block 20 for heat flow in the Z-axis direction. In other implementations it may be desirable to preferentially conduct heat laterally or both laterally and in the Z-axis direction, in which case a different direction of crystal alignment may be desired or the alignment direction may be immaterial to the design. When aluminum is used to dissipate some of the heat, which may be by use of an aluminum heat spreader or an aluminum frame inside the probe housing, it is desirable for the thermal conductivity of the backing block be comparable to or better than that of aluminum, so that heat will preferentially flow to the aluminum. Aluminum has a comparable Tc of 237 W/m° K at room temperature, so this performance objective is well met by a graphite block 20.

A second objective is that the backing block provide structural support for the acoustic stack 100 and integrated circuit 160. A graphite block is structurally sound, satisfying this objective.

A third objective is to provide electrical isolation of the integrated circuit 160 from the aluminum member or frame of the probe. Graphite, being electrically conductive, can satisfy this objective by coating the backing block with a non-conductive insulative coating. In some implementations it may be desirable to coat only the side of the block which is in contact with the transducer stack. In other implementations it may be desirable to coat multiple sides of the backing block. It may be desirable, for instance, to coat the lateral sides of the block with an insulative acoustic damping material which would provide the additional benefit of suppressing lateral acoustic reverberation.

Figure 3:
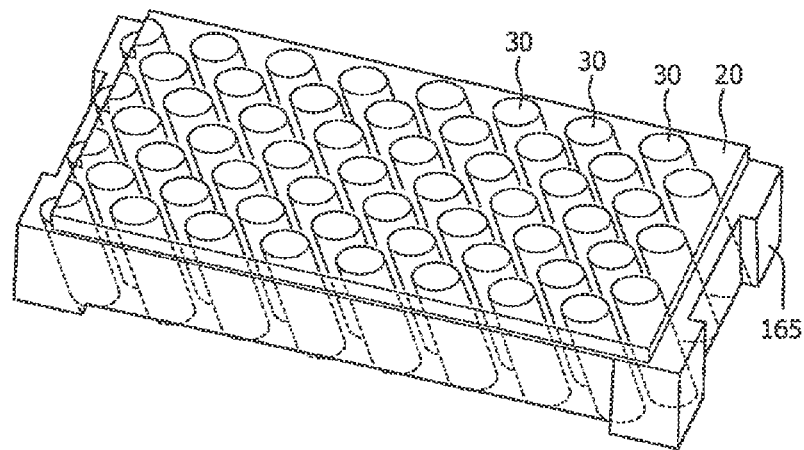
FIG. 3 is a perspective view of a thermally conductive backing block constructed in accordance with the principles of the present invention.
Figure 4:
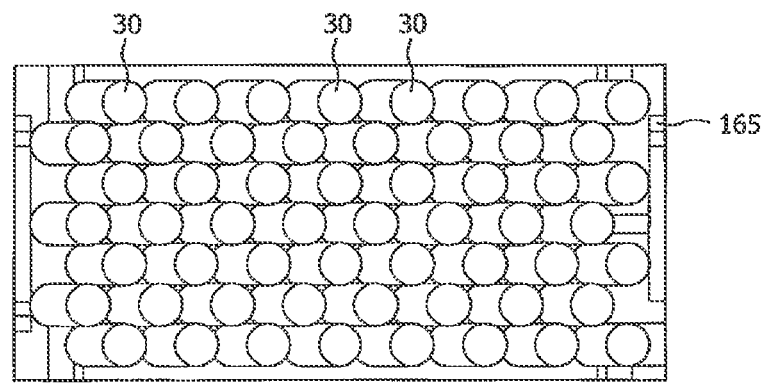
FIG. 4 is a top plan view of a thermally conductive backing block constructed in accordance with the principles of the present invention.
Figure 5:
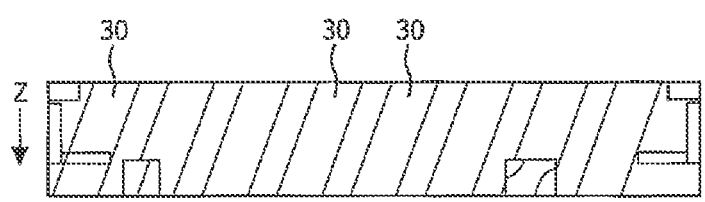
FIG. 5 is a side cross-sectional view of a thermally conductive backing block constructed in accordance with the principles of the present invention.

The fourth objective is that the backing block must dampen acoustic energy entering the block. Graphite is a good conductor of acoustic energy and provides very little inherent acoustic damping. This objective is satisfied by employing the graphite block as the framework for a composite structure of internal acoustic dampening members as shown in FIGS. 3, 4, and 5. In these drawings the graphite is rendered translucent for clarity of illustration of the internal composite structure of the block. The dampening members are formed as a plurality of angled cylinders 30 of backing material in the backing block. The cylinders 30 are cut or drilled into the graphite block 20, then filled with acoustic dampening material such as epoxy filled with micro balloons or other acoustic damping particles. As the top plan view of the backing block of FIG. 4 illustrates, the tops of the cylinders 30 present a large area of acoustic dampening material to the back of the integrated circuit. A considerable amount of the undesired acoustic energy emanating from the back of the integrated circuit and acoustic stack will thus pass immediately into the dampening material. The angling of the cylinders as seen in FIG. 3 and best seen in the cross-section view of FIG. 5 assures that acoustic energy traveling in the Z-axis direction will have to intersect dampening material at some point in the path of travel. Preferably, there is no path in the Z-axis direction formed entirely of graphite, and the angling of the cylinders does not promote reflection of energy back to the integrated circuit but provides scattering angles downward and away from the integrated circuit. In practice it may be sufficient to block most of the Z-axis pathways such as by blocking 95% of the pathways. Thus, the angling of the cylinders assures damping of all or substantially all of the Z-axis directed energy.

Heat, however, will find continuous pathways through the graphite between the cylinders 30. Since the flow of heat is from higher temperature regions to lower (greater thermal density to lesser), heat will flow away from the integrated circuit 160 and acoustic stack 100 to structures below the backing block 165 where it may be safely dissipated.

Figure 6:
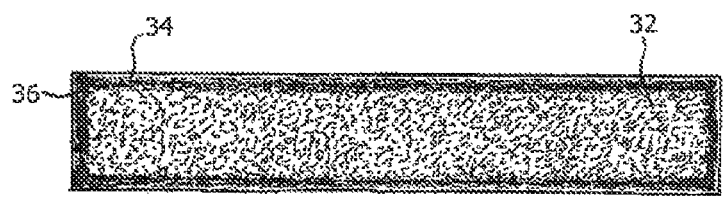
FIG. 6 illustrates a composite foam backing block constructed in accordance with the principles of the present invention.

Other materials may be used for the thermally conductive material of the backing block, such as aluminum, graphite foam, or aluminum nitride. One composite structure which has been found to be advantageous for many applications is a conductive graphite foam filled with epoxy resin. The macroscopic nature of the machined and filled graphite block described above can provide an uneven bonding surface to the ASIC, which is vulnerable to expansion mismatches. the machining and filling of the holes with epoxy is also a labor intensive process. FIG. 6 illustrates an implementation of the present invention in which The backing material of the backing block of FIG. 6 uses a thermally conductive graphite foam (POCO HTC) filled with a soft unfilled attenuating epoxy resin. The unfilled HTC foam has significant porosity (60%), of which 95% of the total porosity is open. When this open porosity is filled with soft resin, this composite backing exhibits a high acoustic attenuation of approximately 50 dB/mm at 5 Mhz. This high attenuation is mainly due to two mechanisms: 1) the absorption of acoustic energy by the soft resin and 2) acoustic energy scattering due to the impedance mismatch between epoxy, graphite, and air in the porous structure. As a result of this high acoustic attenuation, the backing thickness can be reduced to facilitate transducer heat dissipation. Another property of this epoxy filled graphite foam is its high thermal conductivity (~50 W/mK), which is one order of magnitude higher than typical epoxy-filler backing formulations.

Figures 7, 8:
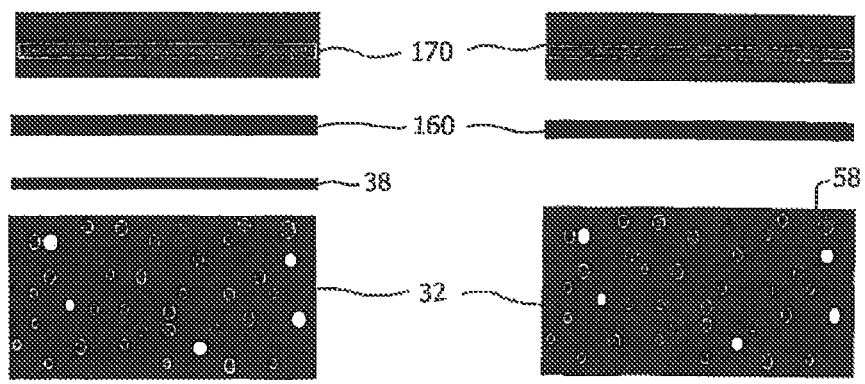
FIG. 7 illustrates an acoustic stack assembly of the present invention with a film insulating layer between the ASIC and a composite foam backing block.
FIG. 8 illustrates an acoustic stack assembly of the present invention with a parylene-coated composite foam backing block.

The composite graphite foam backing block 32 of FIG. 6 illustrates the high porosity of the foam. In this example the surface of the foam block 32 is coated with an epoxy resin 34 which soaks into the block by a depth 36 which is a function of the porosity of the foam block and the viscosity of the resin, as indicated by the shaded areas in the drawing. The cured epoxy gives the block good structural stability. The composite backing block can then be directly bonded to the ASIC 160 with a thin epoxy bondline. In order to provide adequate electrical isolation from the ASIC, an insulating layer can be used between the backing block and the ASIC as illustrated in FIGS. 7 and 8, which show exploded views of two implementations in an acoustic stack. At the top of each drawing is the transducer layer 170 with its matching layers. Below the transducer layer is the ASIC 160. In FIG. 7 a thin (12 to 25 microns) polyimide film 38 is attached to the ASIC before bonding the backing block to the assembly. The composite foam backing block 32 is then bonded to the insulating film 38. In FIG. 8 a parylene coating 58 of 10 to 15 microns is applied to the HTC backing block. The parylene coated backing block is then bonded to the ASIC 160.

What is claimed is:

1. An ultrasonic transducer array assembly comprising:
   an array of transducer elements having a forward desired direction for the transmission of ultrasonic waves and a rearward undesired ultrasonic emission direction;
   an integrated circuit structurally coupled to the array of transducer elements;
   a composite foam backing block located rearward of the array of transducer elements and integrated circuit, the composite foam backing block being formed of a thermally conductive foam material having a porous structure; and
   an unfilled epoxy resin filling a portion of the porous structure of the composite foam backing block, wherein the portion of the porous structure filled with the unfilled epoxy resin extends from a top surface of the composite foam backing block to a depth that is less than a thickness of the composite foam backing block, and wherein the composite foam backing block further comprises cylindrical passages formed in the porous structure of the thermally conductive foam material, wherein the cylindrical passages are arranged at a non-orthogonal angle with respect to the rearward undesired ultrasound emission direction.

2. The ultrasonic transducer array assembly of claim 1, wherein the foam material further comprises a graphite foam.

3. The ultrasonic transducer array assembly of claim 1, wherein the composite foam backing block further comprises an exterior surface, and wherein the epoxy resin fills the porous structure of the foam backing block adjacent to the exterior surface.

4. The ultrasonic transducer array assembly of claim 1, wherein the integrated circuit further comprises a beamformer ASIC coupled to the rearward side of the array of transducer elements, and wherein the composite foam backing block is thermally coupled to the beamformer ASIC.

5. The ultrasonic transducer array assembly of claim 4, further comprising an epoxy bond between the composite foam backing block and the beamformer ASIC, wherein the epoxy bond directly bonds the composite foam backing block to the beamformer ASIC.

6. The ultrasonic transducer array assembly of claim 4, further comprising an electrically insulating layer between the beamformer ASIC and the composite foam backing block.

7. The ultrasonic transducer array assembly of claim 6, wherein the electrically insulating layer further comprises a polyimide film.

8. The ultrasonic transducer array assembly of claim 7, wherein the polyimide film is no thicker than 25 microns.

9. The ultrasonic transducer array assembly of claim 6, wherein the electrically insulating layer further comprises a parylene coating.

10. The ultrasonic transducer array assembly of claim 9, wherein the parylene coating is no thicker than 15 microns.

11. The ultrasonic transducer array assembly of claim 1, wherein the porous structure exhibits a porosity of at least 60%.

12. The ultrasonic transducer array assembly of claim 11, wherein at least 95% of the total porosity of the porous structure is open.

13. The ultrasonic transducer array assembly of claim 1, wherein the thermal conductivity is 50 W/mK.

14. The ultrasonic transducer array assembly of claim 13, wherein the porous foam material further comprises a graphite foam material.

15. The ultrasonic transducer array assembly of claim 1, wherein the unfilled epoxy resin filling a portion of the porous structure is configured to attenuate rearward ultrasonic emissions, wherein the attenuation of rearward ultrasonic emissions is 50 dB/mm at 5 MHz.

16. The ultrasonic transducer array assembly of claim 1, wherein the composite foam backing block includes a coating of an insulative acoustic damping material on at least one lateral side of the composite foam backing block.

17. The ultrasonic transducer array assembly of claim 1, being coupled to a diagnostic ultrasound system.

18. The ultrasonic transducer array assembly of claim 1, wherein the portion of the porous structure filled with the unfilled epoxy resin extends into the composite backing block from a plurality of surfaces of the composite backing block to a depth that is less than a thickness of the composite foam backing block.

19. An ultrasonic transducer array assembly comprising:
   an array of transducer elements having a forward desired direction for the transmission of ultrasonic waves and a rearward undesired ultrasonic emission direction;
   an integrated circuit structurally coupled to the array of transducer elements;
   a composite backing block located rearward of the array of transducer elements and integrated circuit, the composite backing block being formed of a thermally conductive material having a porous structure and including cylindrical passages formed in the porous structure, the cylindrical passages being arranged at a non-orthogonal angle with respect to the rearward undesired ultrasonic emission direction; and
   an epoxy resin filling at least a portion of the cylindrical passages of the composite backing block.

20. The ultrasonic transducer array assembly of claim 19, wherein the material of the composite backing block comprises graphite, the assembly further comprising an electrically isolating layer disposed between the integrated circuit and the composite backing block.

* * * * *